United States Patent
Li et al.

(10) Patent No.: US 11,396,667 B2
(45) Date of Patent: Jul. 26, 2022

(54) ENZYMATIC METHOD FOR PREPARATION OF LECITHIN POLYUNSATURATED FATTY ACIDS (PUFAS)

(71) Applicant: Shaanxi University of Science & Technology, Xi'an (CN)

(72) Inventors: Daoming Li, Xi'an (CN); Kankan Liu, Xi'an (CN); Ning Liu, Xi'an (CN); Junjie Cui, Xi'an (CN)

(73) Assignee: Shaanxi University of Science & Technology

( * ) Notice: Subject to any disclaimer, the term of this patent is extended or adjusted under 35 U.S.C. 154(b) by 137 days.

(21) Appl. No.: 17/085,876

(22) Filed: Oct. 30, 2020

(65) Prior Publication Data

US 2021/0285021 A1    Sep. 16, 2021

(30) Foreign Application Priority Data

Mar. 11, 2020   (CN) .......................... 202010167159.8

(51) Int. Cl.
| | |
|---|---|
| *C12N 9/20* | (2006.01) |
| *C12P 7/6472* | (2022.01) |
| *C11B 1/02* | (2006.01) |
| *C11B 3/00* | (2006.01) |

(52) U.S. Cl.
CPC ............ *C12P 7/6472* (2013.01); *C11B 1/025* (2013.01); *C11B 3/006* (2013.01); *C12N 9/20* (2013.01)

(58) Field of Classification Search
CPC ................................ C12N 9/20; C12P 7/6472
See application file for complete search history.

(56) References Cited

U.S. PATENT DOCUMENTS

2020/0197346 A1\*  6/2020  Russi ..................... A61K 47/26

\* cited by examiner

*Primary Examiner* — Tekchand Saidha
(74) *Attorney, Agent, or Firm* — Brian M. Kaufman; Robert D. Atkins; Patent Law Group: Atkins and Associates, P.C.

(57) ABSTRACT

The disclosure discloses an enzymatic method for preparation of lecithin polyunsaturated fatty acids (PUFAs), and belongs to the technical field of separation and application of enzyme. A heat treatment procedure is added after a reaction substrate is in contact with an enzyme to adjust the ratio of sn-1 lysophospholipid PUFAs to sn-2 lysophospholipid PUFAs in a reaction product and to promote the production of sn-2 lysophospholipid PUFAs, thereby promoting the production of lecithin PUFAs, which greatly increases the production efficiency of lecithin PUFAs and the lecithin PUFA content in the product. With simple operations and high reaction rate, the method can significantly increase the content of lecithin PUFAs in the product, can effectively avoid the oxidation of PUFA, and has high economic benefits and promising industrial application prospects.

10 Claims, No Drawings

ENZYMATIC METHOD FOR PREPARATION OF LECITHIN POLYUNSATURATED FATTY ACIDS (PUFAS)

TECHNICAL FIELD

The disclosure belongs to the technical field of oil processing, and in particular, relates to an enzymatic method for preparation of lecithin polyunsaturated fatty acids (PUFAs).

BACKGROUND

Polyunsaturated fatty acids (PUFAs), such as linoleic acid (C18:2n6), conjugated linoleic acid (CLA) (9c, 11t-C18:2 and 10t, 12c-C18:2), alpha-linolenic acid (ALA) (C18:3n3), gamma-linolenic acid (GLA) (C18:3n6), punicic acid (9c, 11t, 13c-C18:3), stearidonic acid (SDA) (C18:4n3), eicosapentaenoic acid (EPA) (C20:5n3), docosapentaenoic acid (DPA) (C22:5n3) and docosahexaenoicacid (DHA) (C22:6n3), are closely related to human health. Studies have shown that linoleic acid is an essential fatty acid (EFA) for the human body, which plays an important role in lowering blood cholesterol level, preventing atherosclerosis and the like; CLA plays a role in lowering blood lipid level, preventing atherosclerosis, regulating immunity and inflammation and the like; ALA is also an EFA for the human body, which plays a role in anti-inflammation, neuroprotection, preventing cardiovascular diseases and the like; GLA plays a role in lowering blood lipid level, preventing cardiovascular diseases, anti-cancer and the like; punicic acid plays a role in anti-obesity, anti-diabetes, anti-cancer and the like; and SDA, EPA, DPA and DHA can not only contribute to the development of brain, nerves and retinas, but also play a role in anti-inflammation, anti-cancer, preventing cardiovascular diseases and the like. Generally, PUFA mainly exists in the form of free fatty acids, fatty acid ethyl esters (FAEEs), triglycerides (TGs) and phospholipids. PUFA in the form of PL has the highest bioavailability compared with other forms. Therefore, the preparation of phospholipid PUFA has always been a hot research topic. Among phospholipid PUFAs, lecithin PUFAs have attracted more attention than lysophospholipid PUFAs due to higher stability and bioavailability thereof.

Enzymatic acidolysis, enzymatic transesterification and enzymatic esterification are common methods for preparation of lecithin PUFAs. Compared with the preparation of lecithin PUFAs by enzymatic transesterification and enzymatic esterification, the preparation of lecithin PUFAs by enzymatic acidolysis exhibits a higher reaction rate, but lecithin is easily hydrolyzed during the process of preparation of lecithin PUFAs by enzymatic acidolysis, and the incorporation rate of PUFA is low, such that a final product has a lecithin content usually lower than 20% and the lecithin has a PUFA content lower than 60% (Food Chem., 2014, 157: 132-140). The preparation of lecithin PUFAs by enzymatic transesterification exhibits a lower reaction rate than enzymatic acidolysis, a product has a lecithin content usually lower than 20%, and the lecithin has a PUFA content lower than 60%, but PUFA is not easily oxidized during the process of preparation of lecithin PUFAs by enzymatic transesterification, and the product has excellent physical and chemical properties (Catal. Commun., 2016, 75: 60-64). The preparation of lecithin PUFAs by enzymatic esterification needs to be conducted under vacuum, and although lecithin in a product can exhibit an incorporation rate of PUFA up to 90%, the product has a lecithin content usually lower than 5% (Food Chem., 2017, 226: 165-170). In short, for the preparation of lecithin PUFAs by enzymatic acidolysis, enzymatic transesterification and enzymatic esterification at present, products generally have a low lecithin content, and it is hard to obtain a product with both high lecithin content and high PUFA content.

SUMMARY

In order to solve the above problems, the disclosure is intended to provide an enzymatic method for preparation of lecithin PUFAs, which greatly improves the production efficiency of lecithin PUFAs and the lecithin PUFA content in a product by adding a heat treatment procedure after a reaction substrate is in contact with an enzyme.

To achieve the above purpose, the disclosure provides the following technical solution:

An enzymatic method for preparation of lecithin polyunsaturated fatty acids (PUFAs) includes the following steps:

step 1: mixing glycerophosphatidylcholine (GPC) with fatty acids thoroughly;

step 2: reacting a mixed substrate obtained in step 1 with an immobilized lipase under vacuum;

step 3: subjecting a reaction product in step 2 to heat treatment, and then cooling and adding the reaction product to the mixed substrate subjected to reaction in step 2; and step 4: repeating steps 2 and 3 until the reaction reaches equilibrium, and then collecting a reaction product to give lecithin PUFAs.

Preferably, in step 1, the GPC and fatty acids are mixed at a molar ratio of 1:(10-40).

Preferably, in step 2, the immobilized lipase is immobilized Lipozyme TL 100L or MAS1.

Preferably, in step 2, the immobilized lipase is prepared by the following method: mixing a lipase with an immobilization carrier at a lipase-carrier ratio of 40 mg:1 g, and stirring an obtained mixture at 30° C. and 200 rpm for 8 h, wherein, a non-polar macroporous ECR1030 resin is adopted as the immobilization carrier.

Preferably, in step 2, the vacuum refers to a pressure lower than 400 Pa.

Preferably, the reaction in step 2 is conducted in a packed bed reactor.

Preferably, the immobilized lipase is filled in the packed bed reactor at a mass 5% to 10% of the total mass of the mixed substrate; and the contact reaction of the mixed substrate with the immobilized lipase is conducted in the packed bed reactor at 40° C. to 55° C. for 5 min or more.

Preferably, in step 3, the heat treatment is conducted at 60° C. to 70° C. for 20 min to 40 min.

Preferably, the cooling in step 3 refers to cooling to the reaction temperature in step 2.

Preferably, in step 4, after being collected, the reaction product is subjected to column chromatography or solvent extraction to remove by-products.

Compared with the prior art, the disclosure has the following beneficial technical effects.

In the enzymatic method for preparation of lecithin PUFAs disclosed in the disclosure, a heat treatment procedure is added after a reaction substrate is in contact with an enzyme to adjust the ratio of sn-1 lysophospholipid PUFAs to sn-2 lysophospholipid PUFAs in a reaction product and to promote the production of sn-2 lysophospholipid PUFAs, thereby promoting the production of lecithin PUFAs. The method greatly increases the production efficiency of lecithin PUFAs and the lecithin PUFA content in the product. For synthesis of lecithin PUFAs by conventional enzymatic esterification, a product has a lecithin PUFA content lower than 5%. By monitoring the reaction process, it is found that the lower lecithin PUFA content in the product is mainly resulted from the lower content of sn-2 lysophospholipid PUFAs in the reaction mixture, which are template molecules for synthesis of lecithin PUFAs. Therefore, increasing the content of sn-2 lysophospholipid PUFAs in the product mixture will directly affect the content of lecithin PUFAs in the product. Since there is thermodynamic equilibrium between sn-1 lysophospholipid PUFAs and sn-2 lysophospholipid PUFAs, heat treatment can be conducted to adjust the ratio of lysophospholipid PUFA isomers in the product mixture to promote the conversion of sn-1 lysophospholipid PUFAs in the product mixture into sn-2 lysophospholipid PUFAs, thereby increasing the content of sn-2 lysophospholipid PUFAs in the product mixture and thus the production of lecithin PUFAs in the product. With simple operations and high reaction rate, the method can significantly increase the content of lecithin PUFAs in the product, can effectively avoid the oxidation of PUFA, and has high economic benefits and promising industrial application prospects.

Further, glycerophosphatidylcholine (GPC) and fatty acids are used at a molar ratio of 1:(10-40), which is conducive to the production of lysophospholipid PUFAs and lecithin PUFAs in the product.

Further, immobilized Lipozyme TL 100L or MAS1 is adopted as the catalyst, which can effectively promote the conversion of GPC into lysophospholipid PUFAs and lecithin PUFAs.

Further, a non-polar macroporous ECR1030 resin is adopted as an immobilization carrier to immobilize a lipase, which can effectively avoid the encapsulation of GPC on the immobilization carrier during the reaction process, thereby obtaining an immobilized enzyme with high catalytic activity.

Further, the pressure during the reaction is less than 400 Pa, which is more conducive to the removal of water by-products of the reaction and promotes the reaction to proceed in the forward direction.

Further, the immobilized lipase catalyzes the reaction of a mixed substrate in a packed bed reactor, leading to excellent reaction effect and high efficiency, and the immobilized enzyme exhibits high operational stability.

Furthermore, the reaction parameters in the packed bed reactor can effectively promote the production of lysophospholipid PUFAs and lecithin PUFAs, and can allow the immobilized enzyme to retain high operational stability.

Further, heat treatment is conducted at 60° C. to 70° C. for 20 min to 40 min, which can effectively promote the conversion of the configuration of lysophospholipid PUFAs, and can effectively avoid the oxidation of PUFA.

Further, after the heat treatment, the reaction mixture is cooled to the reaction temperature in step 2, which can more effectively promote the conversion of lysophospholipid PUFAs into lecithin PUFAs.

Further, after being collected, a reaction product is subjected to column chromatography or solvent extraction, which can remove excess raw materials and by-products, thereby improving the purity of a final product.

DETAILED DESCRIPTION

The disclosure will be further described below in detail with reference to specific examples, which are listed to explain rather than limit the disclosure. Unless otherwise stated, all percentages refer to mass percentages.

Example 1

10 Kg of PUFA-rich fatty acids (from anchovy oil; EPA: 38.56%, DPA: 6.58%, and DHA: 45.22%) and 0.4 Kg of GPC were added to a material tank, and an obtained mixture was thoroughly stirred under a system with the pressure of 200 Pa. The reaction mixture was delivered to a packed bed reactor via a feeding pump for reaction, where, an immobilized lipase MAS1 (lipase MAS1 was prepared with reference to the method described in Food Chem., 2017, 216: 260-267, and the immobilized lipase MAS1 was prepared according to the method described in the disclosure) was filled at an amount of 1.04 Kg, and the reaction was conducted at 55° C. Then the reaction mixture was subjected to heat treatment in a heat treatment device at 65° C. for 30 min, then cooled to 55° C., and then pumped into the material tank for circulation. The flow rate of the reaction substrate was adjusted so that the contact reaction of the reaction substrate with the immobilized lipase MAS1 was conducted for 5 min in each cycle. 12 h after the circular reaction, samples were taken and detected to give the phospholipid composition of the product. It was found that the product had a lecithin PUFA content of 66.45 mol %, a lysophospholipid PUFA content of 31.12 mol %, and a GPC content of 2.43 mol %; and the lecithin PUFAs in the product had a PUFA content of 89.57% (including 38.47% of EPA, 6.39% of DPA, and 44.71% of DHA).

Example 2

10 Kg of PUFA-rich fatty acids (from anchovy oil; EPA: 38.56%, DPA: 6.58%, and DHA: 45.22%) and 0.2 Kg of GPC were added to a material tank, and an obtained mixture was thoroughly stirred under a system with the pressure of 100 Pa. The reaction mixture was delivered to a packed bed reactor via a feeding pump for reaction (an immobilized lipase Lipozyme TL 100L was filled at an amount of 0.51 Kg, the immobilized lipase Lipozyme TL 100L was prepared according to the method described in the disclosure, and the reaction was conducted at 45° C.). Then the reaction mixture was subjected to heat treatment in a heat treatment device at 60° C. for 40 min, then cooled to 45° C., and then pumped into the material tank for circulation. The flow rate of the reaction substrate was adjusted so that the contact reaction of the reaction substrate with the immobilized lipase Lipozyme TL 100L was conducted for 15 min in each cycle. 12 h after the circular reaction, samples were taken and detected to give the phospholipid composition of the product. It was found that the product had a lecithin PUFA content of 65.86 mol %, a lysophospholipid PUFA content of 31.66 mol %, and a GPC content of 2.48 mol %; and the lecithin PUFAs in the product had a PUFA content of 90.24% (including 38.54% of EPA, 6.69% of DPA, and 45.01% of DHA).

Example 3

10 Kg of PUFA-rich fatty acids (from anchovy oil; EPA: 38.56%, DPA: 6.58%, and DHA: 45.22%) and 0.8 Kg of GPC were added to a material tank, and an obtained mixture was thoroughly stirred under a system with the pressure of 350 Pa. The reaction mixture was delivered to a packed bed reactor via a feeding pump for reaction (an immobilized lipase Lipozyme TL 100L was filled at an amount of 1.08 Kg, the immobilized lipase Lipozyme TL 100L was prepared according to the method described in the disclosure, and the reaction was conducted at 40° C.). Then the reaction mixture was subjected to heat treatment in a heat treatment device at 70° C. for 20 min, then cooled to 40° C., and then pumped into the material tank for circulation. The flow rate of the reaction substrate was adjusted so that the contact reaction of the reaction substrate with the immobilized lipase Lipozyme TL 100L was conducted for 10 min in each cycle. 12 h after the circular reaction, samples were taken and detected to give the phospholipid composition of the product. It was found that the product had a lecithin PUFA content of 63.55 mol %, a lysophospholipid PUFA content of 32.84 mol %, and a GPC content of 3.61 mol %; and the lecithin PUFAs in the product had a PUFA content of 90.26% (including 38.50% of EPA, 6.68% of DPA, and 45.08% of DHA).

Example 4

10 Kg of PUFA-rich fatty acids (from anchovy oil; EPA: 38.56%, DPA: 6.58%, and DHA: 45.22%) and 0.4 Kg of GPC were added to a material tank, and an obtained mixture was thoroughly stirred under a system with the pressure of 300 Pa. The reaction mixture was delivered to a packed bed reactor via a feeding pump for reaction, where, an immobilized lipase MAS1 (lipase MAS1 was prepared with reference to the method described in Food Chem., 2017, 216: 260-267, and the immobilized lipase MAS1 was prepared according to the method described in the disclosure) was filled at an amount of 0.78 Kg, and the reaction was conducted at 50° C. Then the reaction mixture was subjected to heat treatment in a heat treatment device at 65° C. for 30 min, then cooled to 50° C., and then pumped into the material tank for circulation. The flow rate of the reaction substrate was adjusted so that the contact reaction of the reaction substrate with the immobilized lipase MAS1 was conducted for 20 min in each cycle. 12 h after the circular reaction, samples were taken and detected to give the phospholipid composition of the product. It was found that the product had a lecithin PUFA content of 67.82 mol %, a lysophospholipid PUFA content of 30.05 mol %, and a GPC content of 2.13 mol %; and the lecithin PUFAs in the product had a PUFA content of 89.96% (including 38.39% of EPA, 6.59% of DPA, and 44.98% of DHA).

Example 5

10 Kg of PUFA-rich fatty acids (from pomegranate seed oil; punicic acid: 81.77%) and 0.23 Kg of GPC were added to a material tank, and an obtained mixture was thoroughly stirred under a system with the pressure of 150 Pa. The reaction mixture was delivered to a packed bed reactor via a feeding pump for reaction, where, an immobilized lipase MAS1 (lipase MAS1 was prepared with reference to the method described in Food Chem., 2017, 216: 260-267, and the immobilized lipase MAS1 was prepared according to the method described in the disclosure) was filled at an amount of 0.52 Kg, and the reaction was conducted at 50° C. Then the reaction mixture was subjected to heat treatment in a heat treatment device at 70° C. for 20 min, then cooled to 50° C., and then pumped into the material tank for circulation. The flow rate of the reaction substrate was adjusted so that the contact reaction of the reaction substrate with the immobilized lipase MAS1 was conducted for 10 min in each cycle. 12 h after the circular reaction, samples were taken and detected to give the phospholipid composition of the product. It was found that the product had a lecithin PUFA content of 71.66 mol %, a lysophospholipid PUFA content of 26.36 mol %, and a GPC content of 1.98 mol %; and the lecithin PUFAs in the product had a PUFA (punicic acid) content of 81.36%.

Example 6

10 Kg of PUFA-rich fatty acids (from pomegranate seed oil; punicic acid: 81.77%) and 0.92 Kg of GPC were added to a material tank, and an obtained mixture was thoroughly stirred under a system with the pressure of 250 Pa. The reaction mixture was delivered to a packed bed reactor via a feeding pump for reaction (an immobilized lipase Lipozyme TL 100L was filled at an amount of 1.09 Kg, the immobilized lipase Lipozyme TL 100L was prepared according to the method described in the disclosure, and the reaction was conducted at 45° C.). Then the reaction mixture was subjected to heat treatment in a heat treatment device at 60° C. for 40 min, then cooled to 45° C., and then pumped into the material tank for circulation. The flow rate of the reaction substrate was adjusted so that the contact reaction of the reaction substrate with the immobilized lipase Lipozyme TL 100L was conducted for 15 min in each cycle. 12 h after the circular reaction, samples were taken and detected to give the phospholipid composition of the product. It was found that the product had a lecithin PUFA content of 67.77 mol %, a lysophospholipid PUFA content of 29.17 mol %, and a GPC content of 3.06 mol %; and the lecithin PUFAs in the product had a PUFA (punicic acid) content of 81.52%.

Comparative Example 1

10 Kg of PUFA-rich fatty acids (from anchovy oil; EPA: 38.56%, DPA: 6.58%, and DHA: 45.22%) and 0.4 Kg of GPC were added to a material tank, and an obtained mixture was thoroughly stirred under a system with the pressure of 200 Pa. The reaction mixture was delivered to a packed bed reactor via a feeding pump for reaction, where, an immobilized lipase MAS1 (lipase MAS1 was prepared with reference to the method described in Food Chem., 2017, 216: 260-267, and the immobilized lipase MAS1 was prepared according to the method described in the disclosure) was filled at an amount of 1.04 Kg, and the reaction was conducted at 55° C. The flow rate of the reaction substrate was adjusted so that the contact reaction of the reaction substrate with the immobilized lipase MAS1 was conducted for 5 min in each cycle. 12 h after the circular reaction, samples were taken and detected to give the phospholipid composition of the product. It was found that the product had a lecithin PUFA content of 2.43 mol %, a lysophospholipid PUFA content of 90.66 mol %, and a GPC content of 6.91 mol %; and the lecithin PUFAs in the product had a PUFA content of 90.23% (including 38.63% of EPA, 6.47% of DPA, and 45.13% of DHA). Compared with Example 1, this comparative example did not add a heat treatment procedure after the reaction substrate was in contact with the enzyme, and the yield of lecithin PUFAs in the final reaction product was only 2.43 mol %, which was far below the 66.45 mol % in Example 1.

Comparative Example 2

10 Kg of PUFA-rich fatty acids (from pomegranate seed oil; punicic acid: 81.77%) and 0.92 Kg of GPC were added to a material tank, and an obtained mixture was thoroughly stirred under a system with the pressure of 250 Pa. The reaction mixture was delivered to a packed bed reactor via a feeding pump for reaction (an immobilized lipase Lipozyme TL 100L was filled at an amount of 1.09 Kg, the immobilized lipase Lipozyme TL 100L was prepared according to the method described in the disclosure, and the reaction was conducted at 45° C.). The flow rate of the reaction substrate was adjusted so that the contact reaction of the reaction substrate with the immobilized lipase Lipozyme TL 100L was conducted for 15 min in each cycle.

12 h after the circular reaction, samples were taken and detected to give the phospholipid composition of the product. It was found that the product had a lecithin PUFA content of 3.98 mol %, a lysophospholipid PUFA content of 89.88 mol %, and a GPC content of 6.14 mol %; and the lecithin PUFAs in the product had a PUFA (punicic acid) content of 81.75%. Compared with Example 6, this comparative example did not add a heat treatment procedure after the reaction substrate was in contact with the enzyme, and the yield of lecithin PUFAs in the final reaction product was only 3.98 mol %, which was far below the 67.77 mol % in Example 6.

What is claimed is:

1. An enzymatic method for preparation of lecithin polyunsaturated fatty acids (PUFAs), comprising the following steps:
   step 1: mixing glycerophosphatidylcholine (GPC) with fatty acids thoroughly;
   step 2: reacting a mixed substrate obtained in step 1 with an immobilized lipase under vacuum;
   step 3: subjecting a reaction product in step 2 to heat treatment, and then cooling and adding the reaction product to the mixed substrate subjected to reaction in step 2; and
   step 4: repeating steps 2 and 3 until the reaction reaches equilibrium, and then collecting a reaction product to give lecithin PUFAs.

2. The enzymatic method for preparation of lecithin PUFAs according to claim 1, wherein, in step 1, the GPC and fatty acids are mixed at a molar ratio of 1:(10-40).

3. The enzymatic method for preparation of lecithin PUFAs according to claim 1, wherein, in step 2, the immobilized lipase is immobilized Lipozyme TL 100L or MAS1.

4. The enzymatic method for preparation of lecithin PUFAs according to claim 1, wherein, in step 2, the immobilized lipase is prepared by the following method: mixing a lipase with an immobilization carrier at a lipase-carrier ratio of 40 mg:1 g, and stirring an obtained mixture at 30° C. and 200 rpm for 8 h, wherein, a non-polar macroporous ECR1030 resin is adopted as the immobilization carrier.

5. The enzymatic method for preparation of lecithin PUFAs according to claim 1, wherein, in step 2, the vacuum refers to a pressure lower than 400 Pa.

6. The enzymatic method for preparation of lecithin PUFAs according to claim 1, wherein, the reaction in step 2 is conducted in a packed bed reactor.

7. The enzymatic method for preparation of lecithin PUFAs according to claim 6, wherein, the immobilized lipase is filled in the packed bed reactor at a mass 5% to 10% of the total mass of the mixed substrate; and the contact reaction of the mixed substrate with the immobilized lipase is conducted in the packed bed reactor at 40° C. to 55° C. for 5 min or more.

8. The enzymatic method for preparation of lecithin PUFAs according to claim 1, wherein, in step 3, the heat treatment is conducted at 60° C. to 70° C. for 20 min to 40 min.

9. The enzymatic method for preparation of lecithin PUFAs according to claim 1, wherein, the cooling in step 3 refers to cooling to the reaction temperature in step 2.

10. The enzymatic method for preparation of lecithin PUFAs according to claim 1, wherein, in step 4, after being collected, the reaction product is subjected to column chromatography or solvent extraction to remove by-products.

* * * * *